United States Patent [19]

Muller et al.

[11] Patent Number: 5,939,581

[45] Date of Patent: Aug. 17, 1999

[54] PROCESSES FOR PREPARING HYDROCINNAMIC ACID

[75] Inventors: August John Muller; Joseph Stanton Bowers, Jr., both of Mobile, Ala.; John Robert Ira Eubanks, Ocean Springs, Miss.; Carey Cecil Geiger, Gautier, Miss.; John Gabriel Santobianco, Ocean Springs, Miss.

[73] Assignee: First Chemical Corporation, Pascagoula, Miss.

[21] Appl. No.: 08/915,164

[22] Filed: Aug. 20, 1997

[51] Int. Cl.⁶ .............................. C07C 51/16; C07C 51/58
[52] U.S. Cl. .......................... 562/410; 562/861; 562/863; 562/864
[58] Field of Search ................................... 562/410, 861, 562/863, 864

[56] References Cited

U.S. PATENT DOCUMENTS

| | | |
|---|---|---|
| 2,945,050 | 7/1960 | Franke et al. |
| 3,271,445 | 9/1966 | Bartholome et al. |
| 3,520,934 | 7/1970 | Dunkel et al. |
| 4,013,680 | 3/1977 | Johnson et al. |
| 4,094,912 | 6/1978 | Feinstein et al. |
| 4,500,730 | 2/1985 | Tanaka et al. |
| 4,549,025 | 10/1985 | Dalcanale et al. |
| 4,778,924 | 10/1988 | Harada |
| 4,814,494 | 3/1989 | Shimizu et al. |
| 5,614,649 | 3/1997 | Iqbal et al. |
| 5,632,980 | 5/1997 | Konno et al. |

FOREIGN PATENT DOCUMENTS

| | | |
|---|---|---|
| 0 146 373 | 8/1985 | European Pat. Off. |
| 417 496 | 10/1934 | United Kingdom |
| 955421 | 4/1964 | United Kingdom |
| 1 160 725 | 8/1969 | United Kingdom |
| WO 96/11898 | 4/1996 | WIPO |
| WO 96/11900 | 4/1996 | WIPO |

*Primary Examiner*—Brian M. Burn
*Assistant Examiner*—Brian J. Davis
*Attorney, Agent, or Firm*—Alston & Bird LLP

[57] ABSTRACT

Processes for preparing aromatic carboxylic acids. Cinnamaldehyde is hydrogenated to produce a mixture of hydrogenation products, namely, hydrocinnamaldehyde and hydrocinnamic alcohol. The mixture is then oxidized using a suitable oxidizing agent to substantially completely convert both hydrocinnamaldehyde and hydrocinnamic alcohol to hydrocinnamic acid.

11 Claims, No Drawings

PROCESSES FOR PREPARING HYDROCINNAMIC ACID

FIELD OF THE INVENTION

The present invention relates to processes for preparing arylalkyl carboxylic acids, and more particularly to processes for preparing hydrocinnamic acid.

BACKGROUND OF THE INVENTION

Hydrocinnamic acid is used in the preparation of pharmaceuticals, including protease inhibitors used in the treatment of HIV. Conventionally, hydrocinnamic acid is produced by hydrogenating the unsaturated aromatic carboxylic acid cinnamic acid. Hydrocinnamic acid can then be subjected to additional downstream conversions, most notably chlorination to produce hydrocinnamoyl chloride.

Although useful, this synthesis can suffer various drawbacks. Cinnamic acid is relatively expensive. Cinnamic acid also is typically available in limited quantities.

Prior attempts to produce hydrocinnamic acid using alternative syntheses have been largely unsuccessful. For example, published international application Nos. WO 96/11898 and WO 96/11900 are directed to processes in which cinnamaldehyde is hydrogenated to produce hydrocinnamaldehyde, which in turn is oxidized using a medium containing molecular oxygen to produce hydrocinnamic acid. However, hydrogenation of cinnamaldehyde produces a mixture of products, namely hydrocinnamic alcohol in addition to hydrocinnamaldehyde.

The hydrogenation product mixture which includes both hydrocinnamaldehyde and hydrocinnamic alcohol can be oxidized using molecular oxygen as described in the PCT publications. However, the inventors have found that the resultant oxidation product includes undesirable contamination as result of incomplete oxidation of the hydrocinnamic alcohol. Purifying hydrocinnamic acid requires an additional processing step, which can be difficult, time consuming, and expensive. Further, incomplete oxidation of the hydrogenation mixture results in a loss of yield.

SUMMARY OF THE INVENTION

The present invention is directed to processes for the synthesis of hydrocinnamic acid. In the invention, cinnamaldehyde is hydrogenated using conventional hydrogenation techniques. As discussed above, this hydrogenation results in a hydrogenation reaction product which includes a mixture of hydrocinnamaldehyde and hydrocinnamic alcohol.

In contrast to prior techniques, however, in the invention, the hydrogenation product mixture is oxidized under conditions sufficient to substantially completely oxidize both hydrocinnamaldehyde and hydrocinnamic alcohol to produce hydrocinnamic acid. Surprisingly, overoxidation to phenylacetic acid and/or benzoic acid has not been found to be a problem. Preferably, the hydrogenation mixture is oxidized using nitric acid. The oxidization can be conducted using relatively low temperatures, from slightly above room temperature (about 30° C.) and lower.

The process of the invention can provide economies of production because a less expensive and more readily available starting reagent, namely cinnamaldehyde, is used in place of cinnamic acid. Yet despite prior problems such as loss of yield and product purity associated with the use of cinnamaldehyde as a starting reagent, the invention can also provide hydrocinnamic acid with desirable purity without costly, difficult and time consuming purification steps. The present invention also improves yields of hydrocinnamic acid because the hydrogenation product mixture of both hydrocinnamaldehyde and hydrocinnamic alcohol can be substantially completely oxidized. Further, both hydrocinnamaldehyde and hydrocinnamic alcohol in the hydrogenation reaction product mixture can be readily oxidized without requiring heating.

DETAILED DESCRIPTION OF THE INVENTION

Cinnamaldehyde can be hydrogenated using techniques known in the art for hydrogenation of this and other $\alpha,\beta$-unsaturated aldehydes. As the skilled artisan will appreciate, conditions such as temperature and pressure can vary. Preferably, cinnamaldehyde can be hydrogenated at temperatures ranging from about 50° C. to about 250° C., preferably from about 70° C. to about 150° C., although temperatures outside of these ranges can also be used. Pressure generally ranges from about atmospheric pressure to about 1000 psig (pounds per square inch gauge), preferably from about 10 psig to about 250 psig, although again pressures outside of these ranges can also be used. Hydrogenation may also be conducted in the presence of a suitable solvent, such as aliphatic or aromatic hydrocarbons, including hexane, toluene, and the like. An alkali salt of a weak acid can also be added. Representative hydrogenation processes useful in the present invention are described, for example, in U.S. Pat. No. 3,520,934, 4,956,490, and in Rylander's "Hydrogenation Methods." These methods teach techniques to minimize formation of an alcohol which is not critical in this invention.

Conventional hydrogenation catalysts as known in the art can be used, such as palladium (Pd) on a carrier, for example, palladium/carbon (Pd/C) catalysts, Pd/alumina ($AL_2O_3$) catalysts, and the like, although other suitable catalysts such as platinum, nickel, copper, and the like can be used as well. The amount of catalyst used can vary, preferably ranging from about 10 ppm to about 20 weight percent (wt. %) metal, more preferably about 100 ppm to about 5 wt. % metal, relative to the amount of cinnamaldehyde. The reaction product can be removed from the catalyst using conventional techniques.

The resultant reaction product after hydrogenation includes a mixture of compounds, namely, hydrocinnamaldehyde and hydrocinnamic alcohol. In the invention, both hydrocinnamaldehyde and hydrocinnamic alcohol can be readily converted to produce hydrocinnamic acid using oxidizing agents as described herein. Specifically, both hydrocinnamaldehyde and hydrocinnamic alcohol present in the hydrogenation reaction product are converted to hydrocinnamic acid by oxidizing the mixture with a suitable oxidizing agent capable of converting both aldehyde and alcohol to acid without significant overoxidation. In this regard, only trace amounts, if any, of hydrocinnamic alcohol (typically less than about 0.05%) and/or overoxidation byproducts (typically less than about 0.1%) remain. A currently preferred oxidizing agent is nitric acid, although other suitable oxidizing agents capable of oxidizing both aldehyde and alcohol can be used, such as but not limited to, nitric acid plus molecular oxygen, potassium permanganate, chromic acid, and the like. Optionally multiple oxidizing agents may be used in series.

The amount of oxidizing agent used varies, according to the agent selected, operating temperature and pressure, and solvent. For example, nitric acid, having a concentration from about 10% to about 90%, can be used in an amount sufficient to provide a molar ratio of $HNO_3$ to organic ranging from about 2:1 to about 15:1, preferably from about 4:1 to 6:1. Preferably an initiator such as sodium nitrite, copper, oxygen, or the like is used to minimize the induction period.

Oxidization is conducted under conditions of temperature, pressure, time, and the like sufficient to allow substantially complete oxidization of hydrocinnamic alcohol and hydrocinnamaldehyde present in the hydrogenation reaction product. Preferably, the oxidation step is conducted at temperatures from about 0° C. to about 60° C., and more preferably about 5° C. to about 250° C. In addition, preferably, oxidation is conducted at about or above atmospheric pressure for about 0.5 to about 10 hours. An oxidation catalyst is not required, thereby simplifying recovery of the end product.

The oxidation reaction product includes hydrocinnamic acid as well as residual nitric acid and byproducts. The hydrocinnamic acid can be recovered using conventional techniques. For example, the reaction mixture contains two layers, an upper organic layer containing hydrocinnamic acid and a lower layer containing nitric acid. The two layers can be separated by decantation and the organic layer washed with an aqueous solution such as water to remove nitric acid and other water soluble materials therefrom and thereafter the resultant hydrocinnamic acid product can be recovered using conventional techniques.

Surprisingly, the inventors have found that hydrocinnamic acid can be recovered in high yields and desirable purity using cinnamaldehyde as a starting reagent, despite the fact that a mixture of intermediates (namely hydrocinnamaldehyde and hydrocinnamic alcohol) results from hydrogenation of cinnamaldehyde. The process of the invention can provide substantially complete conversion or oxidation of the mixture of hydrogenation products to provide high yields of hydrocinnamic acid. The ratio of hydrocinnamaldehyde to hydrocinnamic alcohol in the hydrogenation reaction product which is oxidized in accordance with invention can vary widely, for example, from about 1:99 to about 99:1. Yet high yields of pure product can be consistently obtained regardless of the ratio of hydrogenation products.

The present invention thus can provide processing advantages. Hydrocinnamic alcohol does not need to be removed from the hydrogenation product. Rather, a mixture of hydrogenation products (hydrocinnamaldehyde and hydrocinnamic alcohol) can be effectively oxidized. Because the mixture of hydrogenation intermediates can be substantially completely oxidized, hydrocinnamic acid can be readily recovered in high yield and purity using simple techniques, thus eliminating time consuming, lengthy, and often ineffective purification techniques which would otherwise be required to remove undesirable byproducts. Further, the present invention can provide economies of production by eliminating the need for a relatively expensive starting reagent with limited availability, namely cinnamic acid.

Hydrocinnamic acid can be used in additional downstream processes, and is particularly advantageous in the production of hydrocinnamoyl chloride, which in turn is a useful intermediate in the production of several pharmaceuticals. Hydrocinnamoyl chloride is particularly useful in the production of protease inhibitors, as described in Tetrahedron Letters, Vol. 33, No. 3, 673–676; J.Med.Chem. 1992, 35, 1685–1701; and Chemistry & Engineering News, May 16, 1994, 6—6, which are useful in the treatment of HIV. Because the hydrocinnamic acid product of the invention can be used in the production of pharmaceuticals, the skilled artisan will appreciate the advantages of the present invention in the production of high purity product.

The present invention will be further illustrated by the following non-limiting examples.

EXAMPLE 1

Hydrogenation

To an autoclave were added 150 g cinnamaldehyde, 150 g toluene, and 0.15 g (dry basis) 5% palladium on carbon catalyst. The autoclave was pressured with hydrogen gas to 120 PSIG and held at 80° C. until the reaction was complete. Catalyst was then removed by filtration. The solution, excluding toluene, was 91% hydrocinnamaldehyde and 8% hydrocinnamic alcohol.

Oxidation

The hydrogenation product solution was added to a mixture of 3.5 g sodium nitrite and 427.5 g 63% nitric acid keeping the temperature under 10° C. The mixture was stirred overnight, then the lower acid layer was discarded. The organic layer was washed with 100 g water, and charged to a rotary evaporator. After the toluene was removed, hydrocinnamic acid of 99.9% purity remained.

Chlorination

To the hydrocinnamic acid were added 0.13 g benzyltriethylammonium chloride and 137.7 g thionyl chloride keeping the reaction temperature at 55–60° C. The resulting hydrocinnamoyl chloride was of 98.5% purity.

EXAMPLE 2

Hydrogenation

To an autoclave were added 75 g cinnamaldehyde, 75 g heptane, and 0.30 g 5% palladium on carbon catalyst. The autoclave was pressured with hydrogen gas to 120 PSIG and held at 80° C. overnight. Catalyst was then removed by filtration. The solution, excluding heptane, was 84% hydrocinnamaldehyde and 14% hydrocinnamic alcohol.

Oxidation

The hydrogenation product solution was added to a mixture of 3.5 g sodium nitrite and 228 g 63% nitric acid keeping the temperature under 10° C. The mixture was stirred until the reaction was complete then the lower acid layer was discarded. The organic layer was washed with 100 g water, charged to a rotary evaporator to remove heptane, and yielded hydrocinnamic acid of 98.9% purity.

Chlorination

To the hydrocinnamic acid were added 0.10 g benzyltriethylammonium chloride and 57.3 g thionyl chloride keeping the reaction temperature at 55–60° C. The resulting hydrocinnamoyl chloride was of 99.0% purity.

EXAMPLE 3

Hydrogenation

To an autoclave were added 225 g cinnamaldehyde, 225 g heptane, and 0.5 g 5% palladium on carbon catalyst. The autoclave was pressured with hydrogen gas to 120 PSIG and held at 100° C. until the reaction was complete. Catalyst was then removed by filtration. The solution, excluding heptane, was 83% hydrocinnamaldehyde and 16% hydrocinnamic alcohol.

Oxidation

The hydrogenation product solution was added to a mixture of 2.25 g sodium nitrite and 684 g 63% nitric acid keeping the temperature under 10° C. The mixture was stirred until the reaction was complete then the lower acid layer was discarded. The organic layer was washed with 100 g water, and 100 g heptane was added before cooling to crystallize the product. Hydrocinnamic acid of 99.9% purity was obtained.

Chlorination

To the hydrocinnamic acid were added 0.10 g benzyltriethylammonium chloride and 156.6 g thionyl chloride, keeping the reaction temperature at 55–65° C. The resulting hydrocinnamoyl chloride was of 99.9% purity.

EXAMPLE 4

Oxidation

To a flask containing 60 g 63% nitric acid was added 20.3 g hydrocinnamaldehyde keeping the temperature under 10° C. The mixture was stirred overnight then 50 g water and 50 g toluene were added, and the acid layer was discarded. The solution, excluding toluene, was 98.2% hydrocinnamic acid.

EXAMPLE 5

Hydrogenation

To an autoclave were added 150 g cinnamaldehyde, 150 g toluene, and 0.15 g 5% palladium on carbon catalyst. The autoclave was pressured with hydrogen gas to 120 PSIG and held at 80° C. until the reaction was complete. Catalyst was then removed by filtration. The solution, excluding toluene, was 91% hydrocinnamaldehyde and 8% hydrocinnamic alcohol.

Oxidation

An aliquot of the hydrogenation product solution weighing 40 g was added to a mixture of 0.5 g sodium nitrite and 100 g 40% nitric acid keeping the temperature under 30° C. The solution, excluding toluene and water, was 73% hydrocinnamic acid. The solution may be substantially completely oxidized in a subsequent oxidation reaction with either nitric acid or another oxidizing agent.

The foregoing examples are illustrative of the present invention and are not to be construed as limiting thereof. The invention is defined by the following claims, with equivalents of the claims to be included therein.

That which is claimed is:

1. A process for preparing hydrocinnamic acid, comprising:

hydrogenating cinnamaldehyde to produce a hydrogenation reaction product comprising hydrocinnamaldehyde and hydrocinnamic alcohol; and oxidizing said hydrogenation reaction product comprising hydrocinnamaldehyde and hydrocinnamic alcohol with an oxidizing agent capable of substantially completely oxidizing both hydrocinnamaldehyde and hydrocinnamic alcohol to produce hydrocinnamic acid without substantial overoxidation.

2. The process of claim 1, wherein said oxidizing agent comprises a reagent selected from the group consisting of nitric acid, nitric acid plus molecular oxygen, potassium permanganate and chromic acid.

3. The process of claim 1, wherein said oxidizing agent comprises nitric acid.

4. The process of claim 3, wherein said oxidizing agent further comprises sodium nitrite, copper or oxygen.

5. The process of claim 3, wherein said oxidizing agent further comprises sodium nitrite.

6. The process of claim 1, wherein said hydrogenation step comprising hydrogenating cinnamaldehyde to produce a hydrogenation reaction product comprising a ratio of hydrocinnamaldehyde:hydrocinnamic alcohol ranging from about 1:99 to about 99:1.

7. The process of claim 1, wherein said oxidation step comprises oxidizing said hydrogenation reaction product at a temperature from about 0° C. to about 60° C.

8. The process of claim 7, wherein said oxidation step comprises oxidizing said hydrogenation reaction product at a temperature of about 5° C. to about 25° C.

9. A process for preparing hydrocinnamic acid, comprising:

hydrogenating cinnamaldehyde to produce a hydrogenation reaction product comprising hydrocinnamaldehyde and hydrocinnamic alcohol; and oxidizing said hydrogenation reaction product comprising hydrocinnamaldehyde and hydrocinnamic alcohol with nitric acid to substantially completely oxidize both hydrocinnamaldehyde and hydrocinnamic alcohol to produce hydrocinnamic acid.

10. A process for preparing hydrocinnamoyl chloride, comprising:

hydrogenating cinnamaldehyde to produce a hydrogenation reaction product comprising hydrocinnamaldehyde and hydrocinnamic alcohol;

oxidizing said hydrogenation reaction product comprising hydrocinnamaldehyde and hydrocinnamic alcohol with nitric acid to substantially completely oxidize both hydrocinnamaldehyde and hydrocinnamic alcohol to produce hydrocinnamic acid; and converting said hydrocinnamic acid to hydrocinnamoyl chloride.

11. A process for preparing HIV protease inhibitors, comprising:

hydrogenating cinnamaldehyde to produce a hydrogenation reaction product comprising hydrocinnamaldehyde and hydrocinnamic alcohol;

oxidizing said hydrogenation reaction product comprising hydrocinnamaldehyde and hydrocinnamic alcohol with nitric acid to substantially completely oxidize both hydrocinnamaldehyde and hydrocinnamic alcohol to produce hydrocinnamic acid;

converting said hydrocinnamic acid to hydrocinnamoyl chloride; and converting said hydrocinnamoyl chloride to HIV protease inhibitors.

* * * * *